United States Patent [19]

Simpson

[11] Patent Number: 5,534,033
[45] Date of Patent: Jul. 9, 1996

[54] ORTHOPEDIC PROSTHETIC IMPLANTS WITH PYROLYTIC CARBON OR CERAMIC ARTICULATING SURFACES

[75] Inventor: Charles L. Simpson, Austin, Tex.

[73] Assignee: CarboMedics, Inc., Austin, Tex.

[21] Appl. No.: 462,955

[22] Filed: Jun. 5, 1995

[51] Int. Cl.$^6$ ................................................. A61F 2/30
[52] U.S. Cl. .................................... 623/18; 623/21
[58] Field of Search ........................... 623/18, 20, 21, 623/22, 23

[56] References Cited

U.S. PATENT DOCUMENTS

| | | | |
|---|---|---|---|
| 3,462,765 | 8/1969 | Swanson | 623/21 |
| 3,886,600 | 6/1975 | Kahn et al. | 623/21 X |
| 3,938,198 | 2/1976 | Kahn et al. | 623/22 |
| 3,990,116 | 11/1976 | Fixel et al. | 623/21 X |
| 4,131,957 | 1/1979 | Bokros | 623/21 X |
| 4,304,011 | 12/1981 | Whelan, III | 623/21 |
| 4,619,659 | 10/1986 | Witzel | 623/23 |
| 4,969,909 | 11/1990 | Barouk | 623/21 |

FOREIGN PATENT DOCUMENTS

| | | | |
|---|---|---|---|
| 0310483 | 4/1989 | European Pat. Off. | 623/21 |
| 1296147 | 3/1987 | U.S.S.R. | 623/21 |

*Primary Examiner*—Mary Beth Jones
*Attorney, Agent, or Firm*—John R. Merkling

[57] ABSTRACT

An orthopedic prosthetic implant having a pyrolytic carbon or ceramic articulating surface and a metallic sheath or shell interfacing with adjacent bone. The articulating surface and shell are attached to one another with a layer of resilient adhesive, such as polymethylmethacrylate (PMMA) which forms a shock absorbing layer between the pyrolytic carbon or ceramic parts and the metal parts. Also, a circumferential seal enclosing two adjacent articulating surfaces on adjacent implant parts. The invention further includes first and second implant parts having mating articulating surfaces, the first and second implant parts being joined by ligament structures. Ligament structures include bands or spring means connecting the first and second implant parts.

9 Claims, 3 Drawing Sheets

ORTHOPEDIC PROSTHETIC IMPLANTS WITH PYROLYTIC CARBON OR CERAMIC ARTICULATING SURFACES

FIELD OF MY INVENTION

My invention relates to orthopedic prosthetic implants which replace articulating surfaces between two bones in a human body, and in particular to orthopedic prosthetic implants having ceramic or pyrolytic carbon articulating surfaces.

BACKGROUND OF MY INVENTION

Orthopedic prosthetic implants are used to replace diseased or impaired joints in the human body. Orthopedic prosthetic implants have been used in joints throughout the body, from fingers, wrists and ankles to knees shoulders and hips. Prosthetic implants are usually implanted on a resected surface of a bone and provide a convex articulating surface to an adjacent bone or a second implant placed on the adjacent bone. In this case, a first implant presents a convex articulating surface to a second implant having a mating concave articulating surface. It is desirable that the two articulating surfaces slide on one another with a low co-efficient of friction. Consequently, low-friction articulating surfaces have been suggested for use in implants. Such surfaces may be metal to metal, with a highly polished surface, metal on ultra high molecular weight polyethylene, or ceramic articulating surfaces. In addition, carbon, and in particular pyrolytic carbon, with or without additional microstructures such as carbon fibers, has been proposed as an articulating surface.

SUMMARY OF MY INVENTION

I have invented an orthopedic prosthetic implant having a pyrolytic carbon or ceramic articulating surface and a metallic sheath or shell interfacing with adjacent bone. The articulating surface and shell are attached to one another with a layer of resilient adhesive, such as polymethylmethacrylate (PMMA) which forms a shock absorbing layer between the carbon or ceramic part and the metal part. My invention also includes a circumferential seal enclosing two adjacent articulating surfaces. My invention further includes first and second implants having mating articulating surfaces, the first and second implants being joined by ligament structures. Ligament structures may include bands or springs connecting the first and second implants.

In view of the foregoing it is an object of my invention to provide an orthopedic prosthetic implant with a pyrolytic carbon articulating surface, conjoined to a shell by a deformable adhesive layer.

It is a further object of my invention to provide an orthopedic prosthetic implant having first and second implant parts and facing articulating surfaces with a seal containing such articulating surfaces.

Another object of my invention is to provide an orthopedic prosthetic implant having first and second implant parts connected by ligament structures.

These and further objects and features of my invention will be apparent from the following detailed description taken with reference to the accompanying drawings.

DETAILED DESCRIPTION

I will now describe my invention in connection with the accompanying drawings, wherein like numerals will be used to designate like parts throughout. I have chosen to describe my invention in connection with an orthopedic prosthetic implant for a human finger joint, but one skilled in the art would be able to apply the teachings and principles of my invention to any orthopedic implant, such as, without limitation, shoulder, ankle, knee or hip prostheses.

Figure 1:
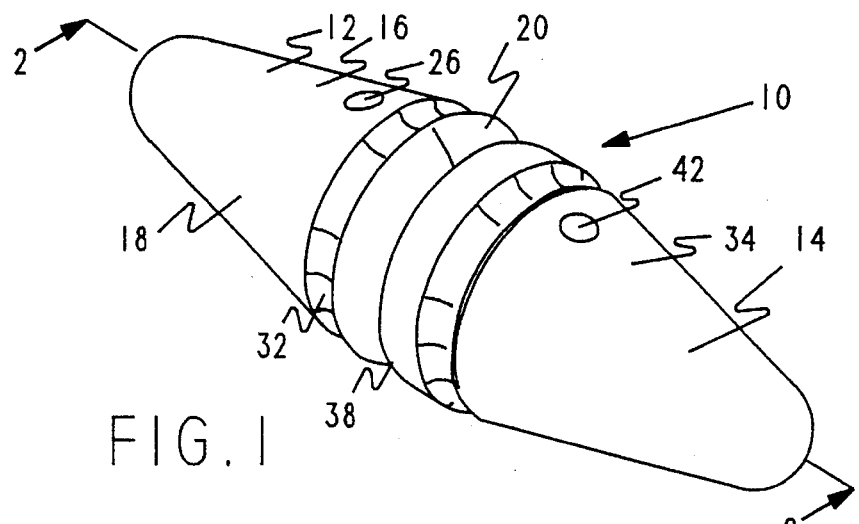
FIG. 1 is a prospective view of an orthopedic prosthetic implant according to my invention for use in the joint of a finger.

FIG. 1 illustrates a perspective view of an orthopedic implant 10 according to my invention. The implant 10 comprises a first implant part 12 adapted to be implanted in a prepared end of a human bone, replacing a part of a joint, and a second implant part 14 adapted to be implanted in a prepared end of a second bone, further replacing the human joint. In the illustrated case, an implant suitable for use in a human finger is illustrated, but, as explained above, other suitable implant configurations for other joints could be used without departing from the teachings of my invention.

The first implant part 12 comprises a shell 16 which will fit in the medullary canal of its implanted bone. The shell 16 is comprised of a suitable biologically compatible material, for example metal, ceramic, hydroxyapatite, or a biologically compatible polymer. Preferably, the shell is a metal such as stainless steel, cobalt chrome alloy, or most preferably, titanium. The shell 16 may have a porous structure or surface 18 to promote adhesion to the adjacent bone. The shell may also be comprised of multiple layers, for example, of an inner layer of cobalt chrome covered by an outer layer of porous titanium. In this connection, see U.S. Pat. No. 5,104,410, the disclosure of which is incorporated herein. Similarly, hydroxyapatite could be applied to a titanium substrate to form the shell.

Figure 2:
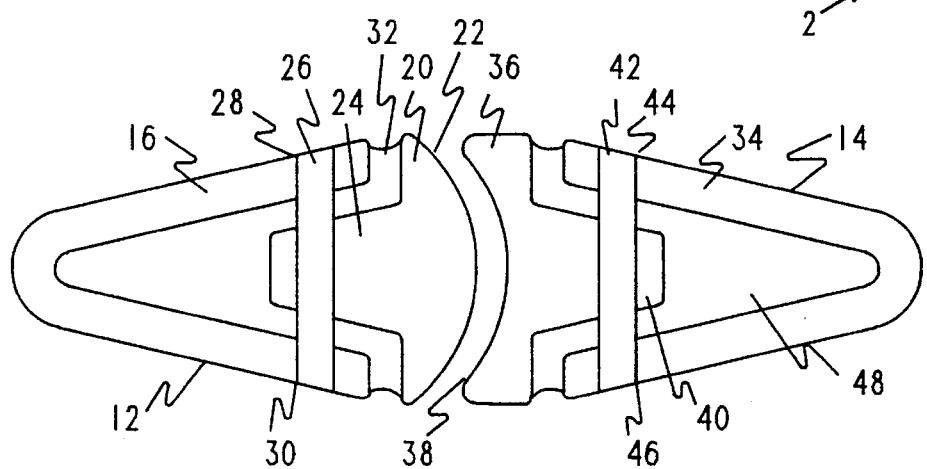
FIG. 2 is a plan through-section of the implant of FIG. 1 taken along the line 2—2.

A convex articulating surface 20 of pyrolytic carbon ceramic such as zirconia or alumina is mounted in the shell 16. As seen in FIG. 2, the convex articulating surface 20 has a curved surface 22 which abuts the second implant part 14. A shaft 24 extends into the shell 16. A pin 26 may be inserted through a bore 28 in the shell 16 through the shaft 24 of the articulating surface 20 and into a second bore 30 in the shell. A bonding layer 32 is provided between the shell 16 and the articulating surface 20. This bonding layer is preferably comprised of a biologically compatible adhesive such as polymethylmethacrylate or another suitable adhesive such as polyamide, polystyrene, vinyl-acrylic, rubber graft polymers and polycarbonate, all of which are frequently used in dental applications, epoxy resin, or cyanoacrylates. A load of adhesive is placed in the shell 16 and then the articulating surface 20 is inserted therein. The pin 26 then fastens the shell and articulating surface together in an appropriate physical relation until the adhesive hardens.

The second implant part 14 is constructed in a like manner to the first implant part 12. The second implant 14 has a similar shell 34 and a concave articulating surface 36. The concave articulating surface 36 has a concave surface 38 which abuts the convex surface 22 in sliding relation. The articulating surface 36 also has a shaft 40 which extends into the shell 34. A second pin 42 extends through a bore 44 in the shell 34 through the shaft 40 and into a second bore 46 in the shell 34. A layer of adhesive 48 is also provided of like form and composition to the layer 32 described above.

Figure 3:
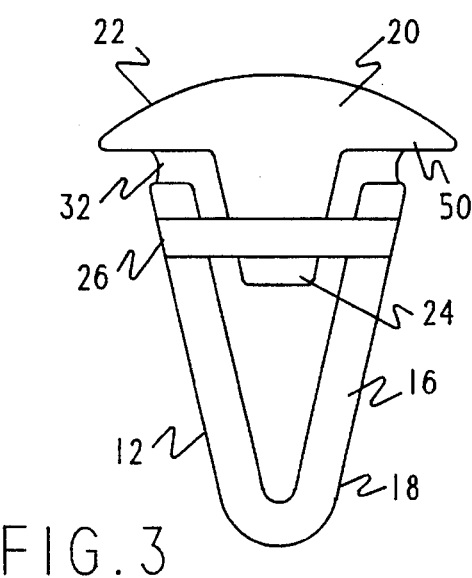
FIG. 3 is a plan perspective view of an alternative second embodiment of my invention.

FIG. 3 shows an alternative embodiment of my invention. I have illustrated the first implant part 12 in through-section with an additional feature. In this embodiment, the articulating 20 is provided with an extended lip 50. The lip 50 enables the implant to be seated against a resected surface of a bone to prevent subsidence of the implant into the bone under chronic load.

Figure 4:
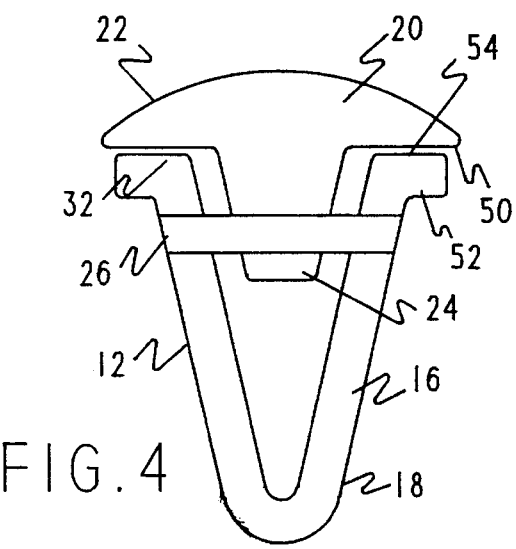
FIG. 4 is a plan perspective view of an alternative third embodiment of my invention.

FIG. 4 illustrates in plan through-section an additional embodiment of my invention. In the embodiment of FIG. 4, the implant part 12 not only has a lip 50 on the articulating surface 20, but an additional flange 52 is provided on the shell 16. This flange 52 again acts to prevent subsidence of the prosthesis by resting against a resected surface of the bone and further provides an area 54 for extended interface between the articulating surface 20 and the shell 16 and particularly between the lip 50 and the flange 52. In this area 54, the adhesive will provide a shock absorbing buffer layer.

Figure 5:
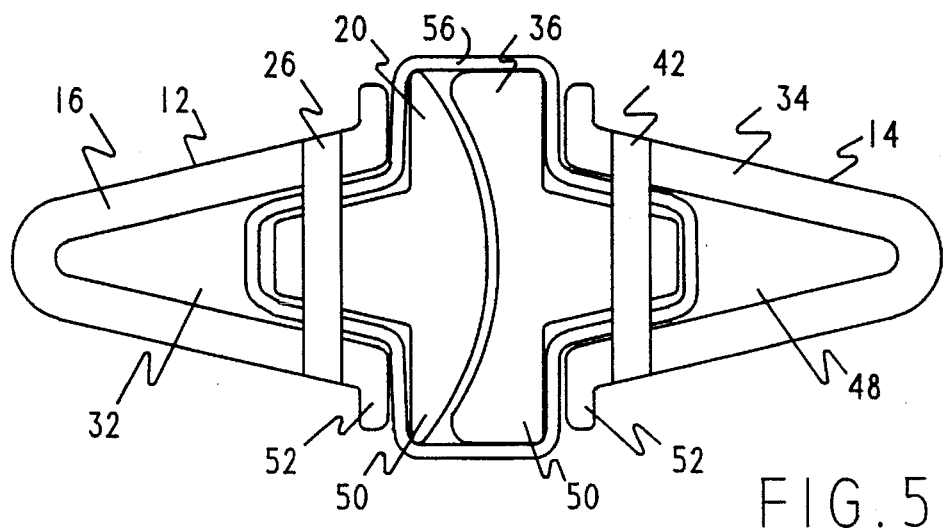
FIG. 5 is a plan perspective view, and through-section, of a fourth embodiment of my invention, having a seal.

A fourth embodiment of my invention is illustrated in plan through-section in FIG. 5. In addition to the features heretofore described, this fourth embodiment further comprises a flexible sheath 56 which encloses the two articulating surface 20, 36. This sheath incases the articulating surfaces to ingrowth around the surfaces. The sheath is comprised of a suitable biologically compatible polymer or material such as knitted Dacron™, or polyester. Polytetrafluoroethylene (PTFE) could also be used as a suitable material.

Figure 6:
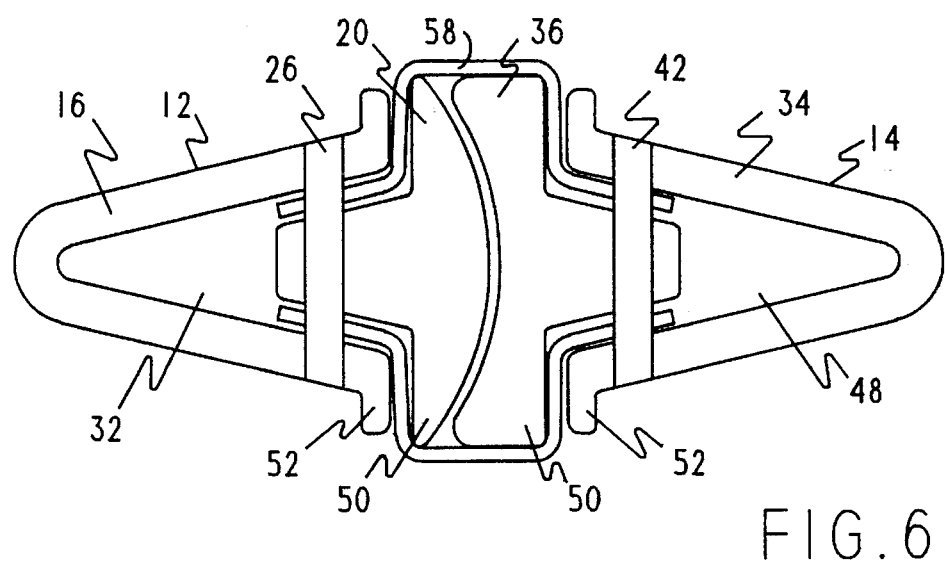
FIG. 6 is a plan view and through-section of a fifth embodiment of my invention, having a second embodiment of the seal.
Figure 7:
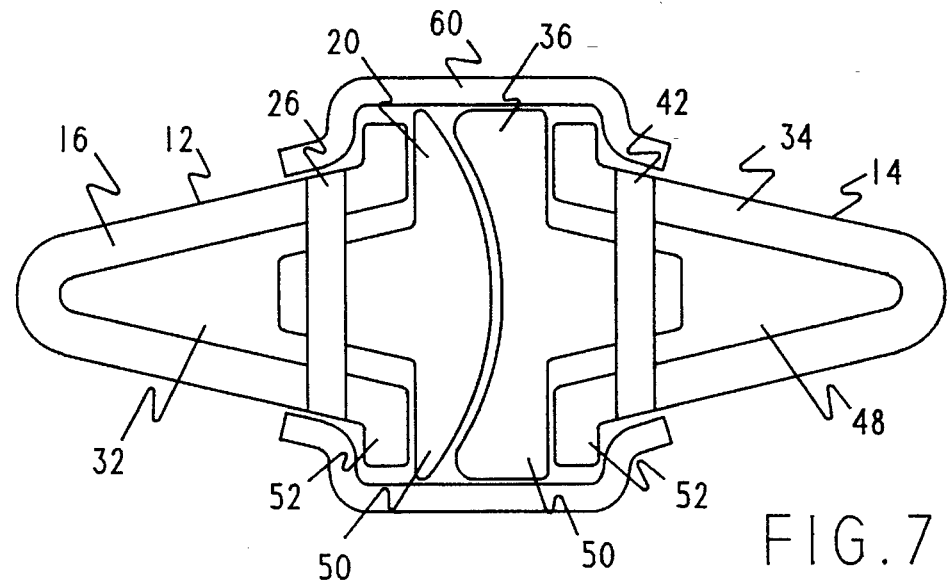
FIG. 7 is a plan view and through-section of a sixth embodiment of my invention, having a third embodiment of the seal.

FIG. 6 illustrates a fifth embodiment, similar to the fourth embodiment of FIG. 5 but having a circumferential sheath 58 which does not fully enclose the articulating surfaces 20, 36. FIG. 7 illustrates a sixth embodiment wherein a sheath 60 is applied outside the articulating surfaces 20, 36 and their adjacent sleeves 16, 34. The sheath 60 is not captured between an articulating surface, such as articulating surface 20 and its adjacent sleeve, 16, but rather is tightly sealed around the sleeve and preferably extends below the flange 52.

Figure 8:
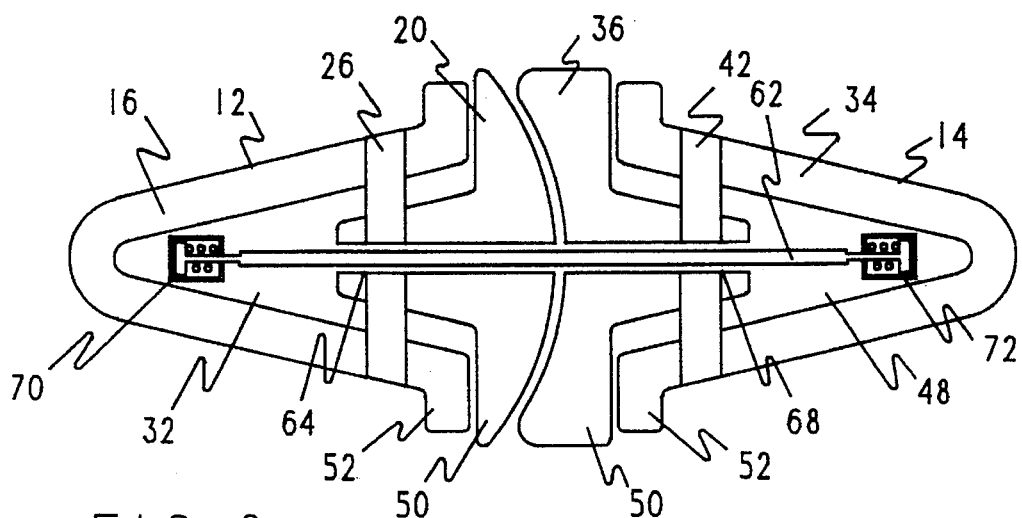
FIG. 8 is the seventh embodiment of my invention having a ligament means connecting a first part and a second part.

Another aspect of my invention is illustrated in plan through-section in FIG. 8. In this seventh embodiment, the first and second implant parts 12, 14 are mechanically joined by ligament means 62. The ligament means 62 comprises a filament 64 of suitable material, such as PTFE, or braided suture material which extends through a bore 64 in the convex articulating surface 20 and into a second bore 66 in the concave articulating surface 36. The ligament means 62 is secured to the shell 16 by a mechanical spring 70. Similarly, a second spring 72 attaches the ligament means 62 to the shell 36. Particularly in small joints, such as finger joints, the ligament means 62 is effective to guide the two implant parts 12, 14 so that they will not disengage.

Figure 9:
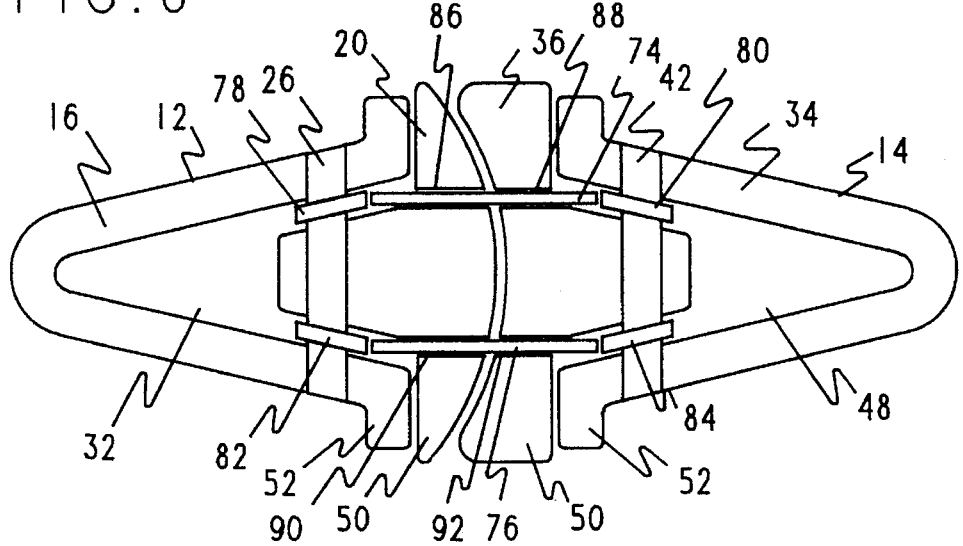
FIG. 9 is the eighth embodiment of my invention, having a second embodiment of ligament means.
Figure 10:
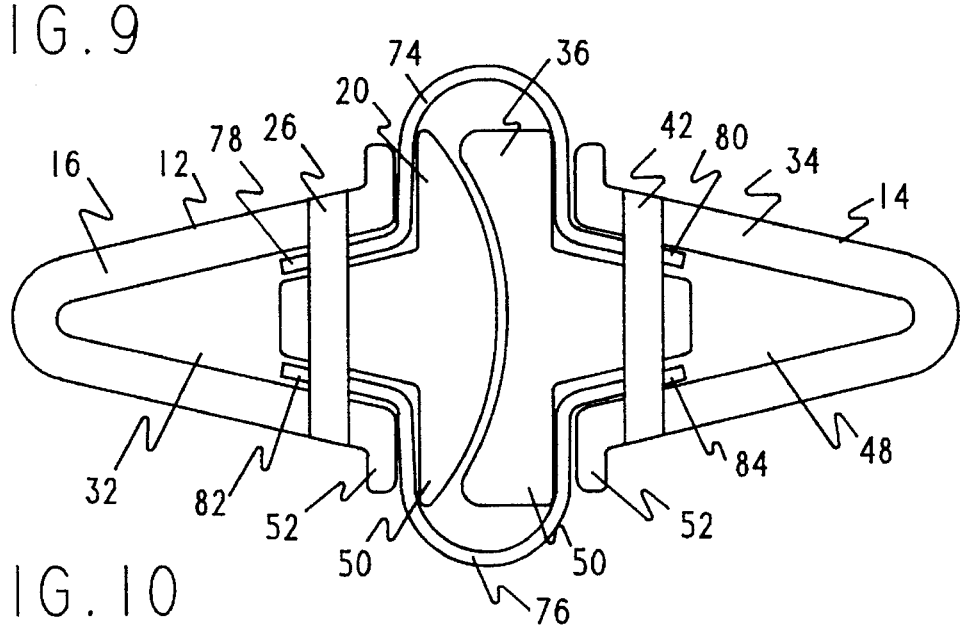
FIG. 10 is the ninth embodiment of my invention having a third embodiment of ligament means.

An alternative eighth embodiment is illustrated in plan through-section in FIG. 9. In this embodiment, two artificial ligaments 74, 76 are provided. These ligaments 74, 76 are attached to the pins 26, 42 by brackets 78, 80 and 82, 84 respectively. In the configuration of FIG. 9, the ligaments 74, 76 are shown passing through bores 86, 88 and 90, 92 in the articulating parts 20, 36 respectively. However, it is also possible to pass the ligaments 74, 76 completely around the articulating surfaces 20, 36 as illustrated in plan view in FIG. 10.

Those skilled in the art will recognize that my invention can be employed in other configurations without departing from the spirit or teachings thereof. The foregoing embodiments are intended, therefore, to be illustrative and not restrictive and the scope of my invention is defined by the following claims.

I claim as my invention:

1. An orthopedic prosthetic implant comprising
    a first implant part, said first implant part having
        a first shell having an exterior surface adapted to lie adjacent bone and an interior surface defining a cavity, said cavity having an opening therein defined by an edge;
        first articulating means comprised essentially of ceramic or carbon, said articulating means having a curved surface for slidingly engaging an opposing surface and having a shaft extending through said opening and into said cavity of said shell; and
        a layer of elastomeric adhesive connecting said shell and said articulating means;
    a second implant part, said second implant part having a second articulating means adapted to slidingly engage said first articulating means, and
    ligament means connecting said first and second implant parts.

2. The orthopedic implant according to claim 1 wherein said ligament means passes through a bore in said first articulating means and through a bore in said second articulating means.

3. The orthopedic implant according to claim 1 wherein said ligament means is attached to at least one of said parts with a spring means.

4. The orthopedic implant according to claim 3 wherein said ligament means passes through a bore in said first articulating means and through a bore in said second articulating means.

5. The orthopedic implant according to claim 1 wherein said ligament means passes around said articulating means.

6. The orthopedic implant according to claim 1 wherein said first articulating means further comprises an lip extending over said edge of said shell; wherein said edge of said shell comprises a flange extending outwardly from said exterior surface of said shell, adjacent said lip; and wherein said ligament means passes between said lip and said flange and around said articulating means.

7. An orthopedic prosthetic implant comprising a first implant part, said implant part having first articulating means having a concave curved surface, and a second implant part, said second implant part having a second articulating means having a convex curved surface adapted to slidingly engage said concave surface of said first articulating means, and ligament means connecting said first and second implant parts, said ligament means being attached to at least one of said parts with a spring means.

8. The orthopedic implant according to claim 7 wherein said ligament means passes through a bore in said first articulating means and through a bore in said second articulating means.

9. An orthopedic prosthetic implant comprising at least one implant part, said implant part having a first shell having an exterior surface adapted to lie adjacent bone and an interior surface defining a cavity, said cavity having an opening therein defined by a flange extending outwardly from said exterior surface of said shell;

first articulating means comprised essentially of ceramic or carbon, said articulating means having a curved surface for slidingly engaging an opposing surface and having a shaft extending through said opening and into said cavity of said shell and a lip extending over said flange of said shell; and a layer of elastomeric adhesive connecting said shell and said articulating surface.

* * * * *